United States Patent
Qi et al.

(10) Patent No.: US 12,180,528 B2
(45) Date of Patent: Dec. 31, 2024

(54) STRAIN FOR PRODUCING LIPASE AND APPLICATION THEREOF

(71) Applicant: CHANGSHU INSTITUTE OF TECHNOLOGY, Suzhou (CN)

(72) Inventors: Bin Qi, Suzhou (CN); Limei Wang, Suzhou (CN); Manting Qi, Suzhou (CN); Tiantian Xu, Suzhou (CN); Yamei Ji, Suzhou (CN); Zhenghong Li, Suzhou (CN)

(73) Assignee: CHANGSHU INSTITUTE OF TECHNOLOGY, Suzhou (CN)

( * ) Notice: Subject to any disclaimer, the term of this patent is extended or adjusted under 35 U.S.C. 154(b) by 350 days.

(21) Appl. No.: 17/754,062

(22) PCT Filed: Oct. 31, 2019

(86) PCT No.: PCT/CN2019/114830
§ 371 (c)(1),
(2) Date: Mar. 23, 2022

(87) PCT Pub. No.: WO2021/056683
PCT Pub. Date: Apr. 1, 2021

(65) Prior Publication Data
US 2022/0333149 A1    Oct. 20, 2022

(30) Foreign Application Priority Data

Sep. 27, 2019 (CN) .......................... 201910926645.0

(51) Int. Cl.
| | |
|---|---|
| *C12P 23/00* | (2006.01) |
| *C12N 1/20* | (2006.01) |
| *C12P 7/6436* | (2022.01) |
| *C12R 1/125* | (2006.01) |

(52) U.S. Cl.
CPC .............. *C12P 23/00* (2013.01); *C12N 1/205* (2021.05); *C12P 7/6436* (2013.01); *C12R 2001/125* (2021.05)

(58) Field of Classification Search
CPC ...... C12P 23/00; C12R 2001/125; C12N 1/20
See application file for complete search history.

(56) References Cited

FOREIGN PATENT DOCUMENTS

| | | | |
|---|---|---|---|
| CN | 108865928 A | * 11/2018 | ............. A23K 10/12 |
| CN | 109777793 A | *  5/2019 | ............... C12N 9/20 |

OTHER PUBLICATIONS

Yang, et al. Biotechnology and Bioengineering. 2019; 116:745-756 (Year: 2019).*
Liu, et al. J. Agric. Food Chem. 2019, 67, 3, 836-843 (Year: 2019).*
Soeka, et al. G.J.B.A.H.S.,2014, vol. 3(1):205-210 (Year: 2014).*
Thu, et al. ASEAN Journal on Science and Technology for Development: 2017, vol. 25: No. 2, Article 17 (Year: 2017).*
Hu, et al. Process Biochemistry, 2022, vol. 114, pp. 59-65 (Year: 2022).*
Liu, et al. Microbiological Research 167 (2012) 452-460 (Year: 2012).*
Puri, et al. J Food Sci Technol (Dec. 2015) 52(12):8228-8235 (Year: 2015).*

* cited by examiner

*Primary Examiner* — Louise W Humphrey
*Assistant Examiner* — Jessica Faye Edwards
(74) *Attorney, Agent, or Firm* — Proi Intellectual Property US

(57) ABSTRACT

The present invention relates to a lipase-producing strain and application thereof. The strain is classified and named *Bacillus subtilis* CS1802, with a preservation number of CCTCC NO: M2018262. The strain can be used to produce vitamin A palmitate through whole-cell transformation of vitamin A and palmitic acid. The *Bacillus subtilis* CS1802 of the present invention is derived from traditional natural fermented food and is a microorganism generally recognized as safe. The strain can be easily cultured and preserved. The highest content of vitamin A palmitate obtained through whole-cell transformation of vitamin A and palmitic acid is 15.35 mg/L. The highest transformation efficiency is 76.75%. The strain provides a new path for enzymatic synthesis of vitamin A palmitate and has important application prospects.

6 Claims, 3 Drawing Sheets

Specification includes a Sequence Listing.

STRAIN FOR PRODUCING LIPASE AND APPLICATION THEREOF

TECHNICAL FIELD

The present invention relates to a lipase-producing strain and its application in enzymatic synthesis of vitamin A palmitate and pertains to a technology in the industrial microbial field.

BACKGROUND ART

Vitamin A palmitate is one of the most commonly and widely used vitamin A series products. Vitamin A palmitate can not only help maintain a normal visual function but also participate in various metabolic activities to maintain the health of the organism. Generally it is used as an additive in food, cosmetics and medicine industries. At present, vitamin A palmitate is synthesized mainly by chemical and enzymatic methods. The chemical synthesis of vitamin A palmitate has problems such as environmental pollution and equipment corrosion, while the enzymatic method has less pollution, a higher space-time yield and a lower cost. Therefore, the research on the technology for enzymatic synthesis of vitamin A palmitate is getting more active.

*Bacillus subtilis* lipase mainly includes LipA and LipB. Numerous studies have shown that LipA can hydrolyze long-chain fatty acids. LipA does not have a lid subdomain and has a small molecular weight, so it is considered as one of the smallest α/β folding hydrolases. Through structural comparison, it is found that the structure of LipA is very similar to that of lipase B derived from *Candida antarctica*, while the current enzymatic synthesis of vitamin A palmitate mostly uses Novozymes 435 (*Candida antarctica* lipase B) immobilized enzyme, but this enzyme is expensive and the cost of its industrial production and application is too high. Opossum shrimp paste is mainly produced by natural fermentation of marine opossum shrimp with salt for about a month. It is rich in protein, chitin and fat. It is a popular seasoning in China and Southeast Asia region. Opossum shrimp paste has very complex microbial diversity and composition and is suitable for screening lipase-producing strains. At present, there is no report of screening a lipase-producing strain from opossum shrimp paste and using this strain to develop an organic phase whole-cell transformation method to produce vitamin A palmitate.

SUMMARY OF THE INVENTION

The first object of the present invention is to provide a lipase-producing strain.

In order to achieve the foregoing technical object of the present invention, the present invention adopts the following technical solution:

A lipase-producing strain, classified and named *Bacillus subtilis* CS1802, preserved in China Center for Type Culture Collection, address: Wuhan University, Wuhan, China; deposit number: CCTCC M2018262; deposit date: May 10, 2018.

The deposits were made and accepted under the Budapest Treaty and applicant avers under 37 CFR $1.808 (a) that the deposit was made under conditions that assure that:

(1) Access to the deposit will be available during pendency of the patent application making reference to the deposit to one determined by the Director to be entitled thereto under $1.14 and 35 U.S.C. § 122, and (2) Subject to paragraph (b) of this section, all restrictions imposed by the depositor on the availability to the public of the deposited material will be irrevocably removed upon the granting of the patent.

The foregoing strain was separated from naturally fermented opossum shrimp paste by the Center of Fermentation Engineering, Changshu Institute of Technology.

*Bacillus subtilis* CS1802 in the present invention has the following physicochemical properties:

Morphology: After growing on a screening medium for 1 d, distinct colonies can be formed. The colonies are irregular or wrinkled in shape, Gram-positive bacteria, baculiform.

Culture characteristics: The optimum temperature for growth is about 30° C., aerobic; and the optimum pH value for growth is about 7.

Another object of the present invention is to provide an application of the foregoing strain in enzymatic synthesis of vitamin A palmitate.

The present invention provides an application method for producing vitamin A palmitate by the whole-cell transformation method, which specifically comprises steps of:

(1) inoculating the strain CS1802 into a beef extract peptone liquid medium for shake culture;

(2) inoculating the strain cultured at the step (1) into a fermentation medium for shake fermentation; centrifuging the fermentation broth, discarding the precipitate and collecting the supernatant, i.e., the fermented bacterial solution.

(3) centrifuging the fermented bacterial solution and inoculating the bacteria into an organic phase system for fermentation to produce vitamin A palmitate.

Further, the temperature of shake culture and fermentation culture is 30° C.

Further, the composition of the fermentation medium is as follows:

Tryptone 10 g/L, yeast powder 5 g/L, NaCl 10 g/L, $MgSO_4 \cdot 7H_2O$ 1 g/L, $KH_2PO_4$ 0.5 g/L, $K_2HPO_4$ 0.5 g/L, and olive oil emulsion 12 mL/L. The olive oil emulsion preparation method is as follows: mixing the olive oil emulsifier PVA and olive oil at a volume ratio of 3:1 and emulsifying them by ultrasound.

Further, the organic phase system is vitamin A and palmitic acid dissolved in an organic solvent according to a mass ratio of 1:1; the concentration of vitamin A and palmitic acid is 10~25 g/L, preferably 15 g/L. The organic solvent is preferably n-hexane.

Further, the bacteria are inoculated into the organic phase system and fermented for 0.5~2 h; preferably 1 h.

The present invention provides *Bacillus subtilis* that can be used for enzymatic synthesis of vitamin A palmitate; this strain is derived from traditional natural fermented food and has broad application prospects in the food industry; the strain grows well on the beef extract peptone solid medium and can be easily cultured and preserved. Through the whole-cell transformation method, under the condition of 15 g/L vitamin A and palmitic acid substrate concentration, the yield of vitamin A palmitate is 15.35 mg/mL and the transformation rate is 76.75%.

Figure 1:
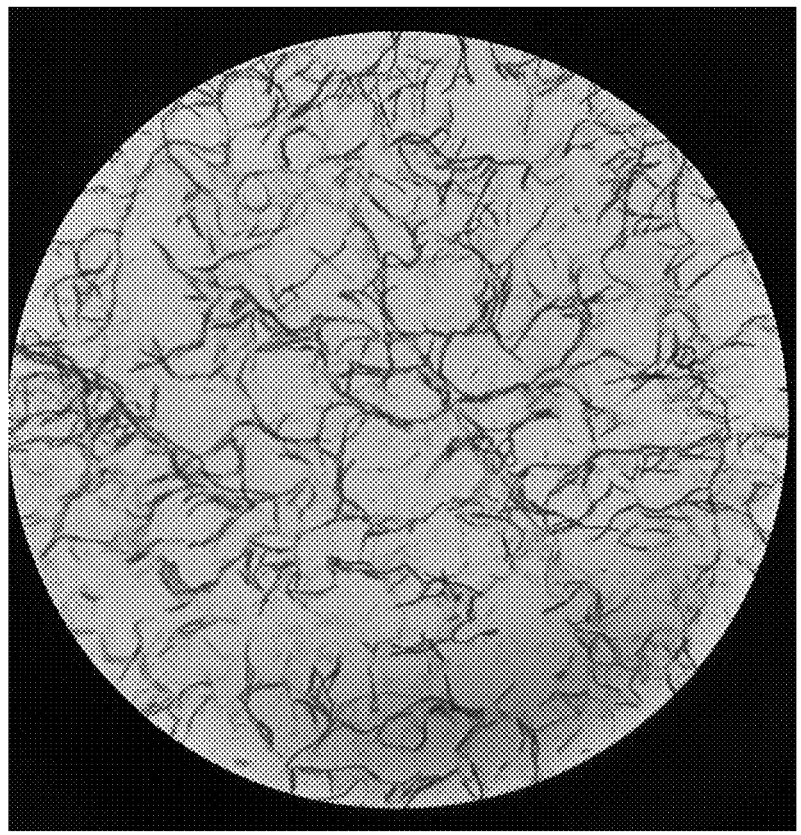
FIG. 1 shows the microscopic morphology of *Bacillus subtilis* CS1802 after Gram staining.

The biological material that the present invention relates to is classified and named: *Bacillus subtilis* CS1802 and preserved in China Center for Type Culture Collection ("CCTCC" for short), address: Wuhan University, Wuhan, China; preservation No. CCTCC NO: M2018262; preservation date: May 10, 2018.

DETAILED DESCRIPTION

Embodiment 1

This embodiment describes the screening, purification and identification methods of *Bacillus subtilis* CS1802.

The screening sample is opossum shrimp paste from Lianyungang Haiwa Food Co., Ltd. Weigh 25 g of shrimp paste, make it and 225 mL of normal saline into a bacterial suspension and dilute the bacterial suspension to $10^{-1}$, $10^{-}$, $10^{-3}$ and $10^{-4}$ of the original concentration, respectively. Spread the bacterial suspension stock solution and $10^{-1}$ diluted, $10^{-2}$ diluted, $10^{-3}$ diluted and $10^{-4}$ diluted bacteria solutions on a primary screening medium, pick a well-grown single colony after growth at 30° C. for 1~2 d and streak on the primary screen medium for isolation. Pick a single colony produced on the primary screening medium and having a clear transparent zone around it, inoculate it into a secondary screening medium, and culture it on a 30° C., 200 r/min shaker for 1-2 d.

The primary screening medium: peptone 10 g/L, yeast powder 5 g/L, NaCl 10 g/L, tributyrin 2 mL/L, agar powder 20 g/L, and distilled water to a constant volume of 1,000 mL.

The secondary screening medium: tryptone 10 g/L, yeast powder 5 g/L, NaCl 10 g/L, MgSO$_4$.7H$_2$O 1 g/L, KH$_2$PO$_4$ 0.5 g/L, K$_2$HPO$_4$ 0.5 g/L, olive oil emulsion 12 mL/L and distilled water to a constant volume of 1,000 mL. The olive oil emulsion preparation method is as follows: mixing the olive oil emulsifier PVA and olive oil at a volume ratio of 3:1 and emulsifying them by ultrasound.

Pick a loop of bacteria from the primary screening medium plate and mix it with a water droplet on the slide and overheat it. Perform primary staining with crystal violet, enzymatic staining with an iodine solution, decolorization with ethanol and counterstaining with safranine and examine under a microscope. The bacteria are Gram-positive bacteria (FIG. 1).

The physicochemical properties of this strain are as follows:

Morphology: After growing on a screening medium for one day, distinct colonies can be formed. The colonies are irregular or wrinkled in shape, Gram-positive bacteria, baculiform.

Physiological and biochemical characteristics: 7% NaCl growth, citrate utilization, oxidase, contact enzyme, V-P test and starch hydrolysis are all positive; carbon sources such as sucrose, maltose, rhamnose, raffinose, glucose, N-acetylglucosamine and colloidal chitin can be utilized.

Culture characteristics: The optimum temperature for growth is about 30° C., aerobic; and the optimum pH value for growth is about 7.

Figure 2:
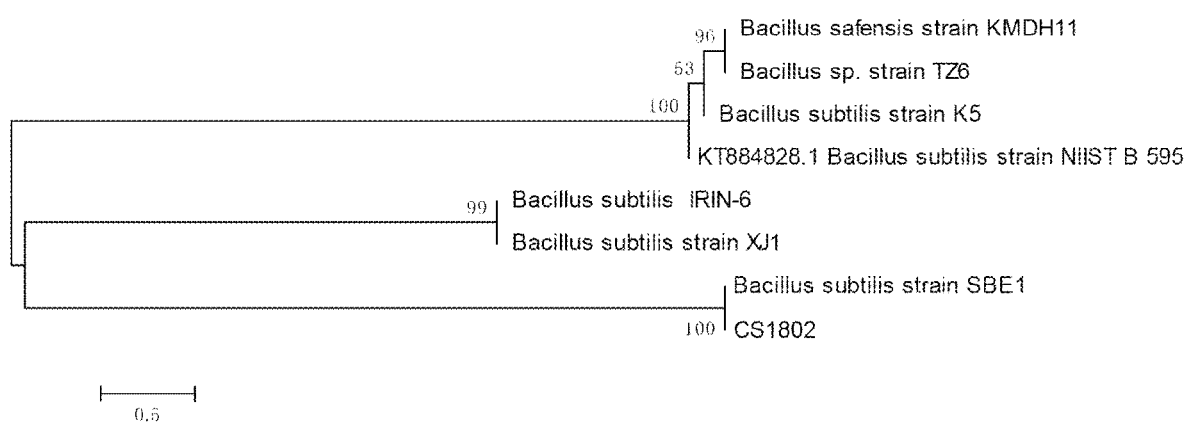
FIG. 2 is a phylogenetic tree of *Bacillus subtilis* CS1802.

The 16S rDNA part of the foregoing strain was subject to sequence determination and BLAST comparison. Then an N-J phylogenetic tree was established using MEGA 5.1 for analysis. Its 16SrDNA sequence is as shown in SEQ ID NO: 1 and its phylogenetic tree is as shown in FIG. 2, so it is identified as *Bacillus subtilis*. After the identification and preservation according to the microbial preservation procedures, it is classified and named *Bacillus subtilis* CS1802. Its preservation number is CCTCC NO: M2018262.

Embodiment 2

This embodiment specifically describes the application of the strain CS1802 in the production of lipase by fermentation of olive oil.

(1) inoculating the strain CS1802 into a beef extract peptone liquid medium for shake culture at 30° C. for 18~24 h;

(2) inoculating the strain cultured at the step (1) in an inoculum size of 2% into a fermentation medium for shake culture at 30° C. for 14~24 h; and centrifuging the fermentation broth, discarding the precipitate and collecting the supernatant. The determined enzyme activity of lipase was 214.3 U/L.

The composition of the fermentation medium is the same as that of the foregoing secondary screening medium.

The method for determining the enzyme activity of lipase: Centrifuge the fermentation broth at 3,000 r for 10 min, collect the supernatant as a sample to be tested, add the sample to be tested and horse radish peroxidase (HRP)-labeled detection antibody in turn into micropores coated with lipase in advance, incubate at 37° C. for 1 h and wash thoroughly. Develop with a substrate 3,3',5,5'-tetramethyl benzidine (TMB), transform it into blue under the catalysis of HRP and transform it into ultimate yellow under the action of acid. Determine the OD value by ELIASA at 450 nm wavelength and calculate the sample activity from a standard curve. The standard substances are 0, 1.5, 3, 6, 12, 24 U/L enzyme solutions prepared with pure lipase. Definition of enzyme activity: The amount of enzyme that causes 1 mg of protein to decompose the substrate to produce 1 µmol of fatty acid per hour under the condition of 37° C. is one enzyme activity unit U. The lipase ELISA assay kit was purchased from Wuhan Chundu Biotechnology Co., Ltd.

Embodiment 3

This embodiment specifically describes the application of the strain CS1802 in the production of vitamin A palmitate through whole-cell transformation.

(1) inoculating the strain CS1802 into a beef extract peptone liquid medium for shake culture at 30° C. for 18~24 h;

(2) inoculating the strain cultured at the step (1) in an inoculum size of 2% into a fermentation medium for shake culture at 30° C. for 14~24 h; and centrifuging the fermentation broth, discarding the precipitate and collecting the supernatant.

Figure 3:
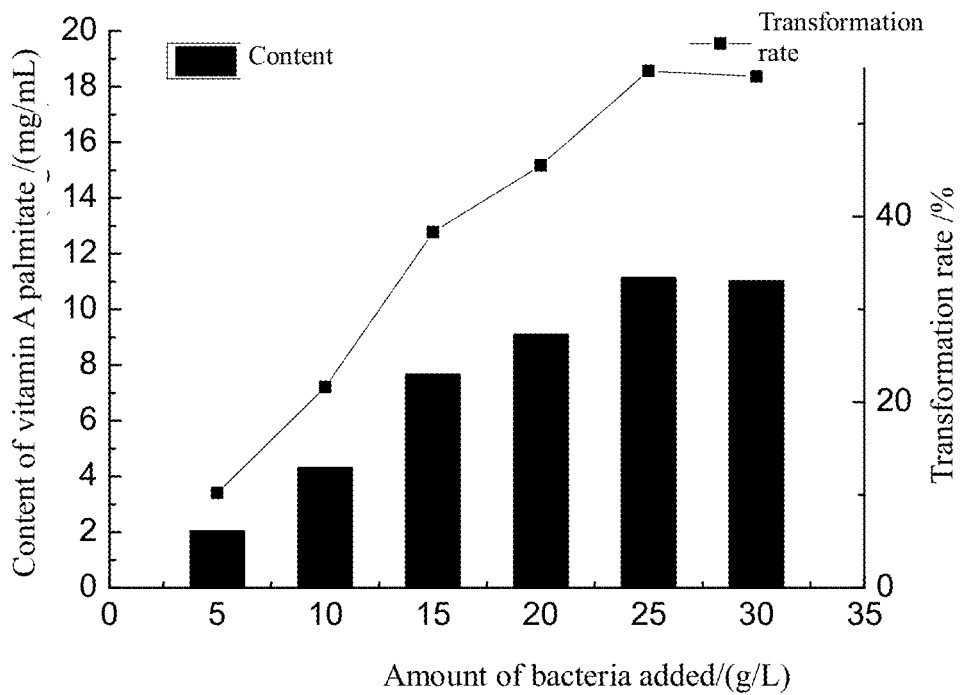
FIG. 3 shows the amount of transformed bacteria added for production of vitamin A palmitate from *Bacillus subtilis* CS1802 by the whole-cell method.

(3) centrifuging the fermented bacterial solution at 3,000 r/min for 5 min, inoculating the bacteria at 5 g/L, 10 g/L, 15 g/L, 20 g/L, 25 g/L and 30 g/L into an organic phase system (vitamin A: palmitic acid=10 g: 10 g dissolved in 1 L of n-hexane) for fermentation for 2 h, then determining the content of vitamin A palmitate and calculating the transformation rate. From FIG. 3, it can be known that when the amount of bacteria added was 25 g/L, the highest transformation efficiency was 55.7%, and the content of vitamin A palmitate was 11.14 mg/L.

The composition of the fermentation medium is the same as that of the foregoing secondary screening medium.

The method for determining vitamin A palmitate: HPLC, and external standard method for quantification. The chromatographic conditions are: Column: Alltech $C_{18}$ (250×4.6 mm, 4.5 μm); mobile phase: 100% methanol; detector: Shimadzu 10A UV detector; detection wavelength: 327 nm; flow rate: 1 mL/min.

The formula for calculating the transformation rate is:

$$\text{Transformation rate} = \frac{\text{Vitamin } A \text{ palmitate (g/L)}}{(\text{Vitamin } A \text{ (g)} + \text{palmitic acid (g)})/n-\text{hexane (L)}} \times 100\%.$$

Embodiment 4

Figure 4:
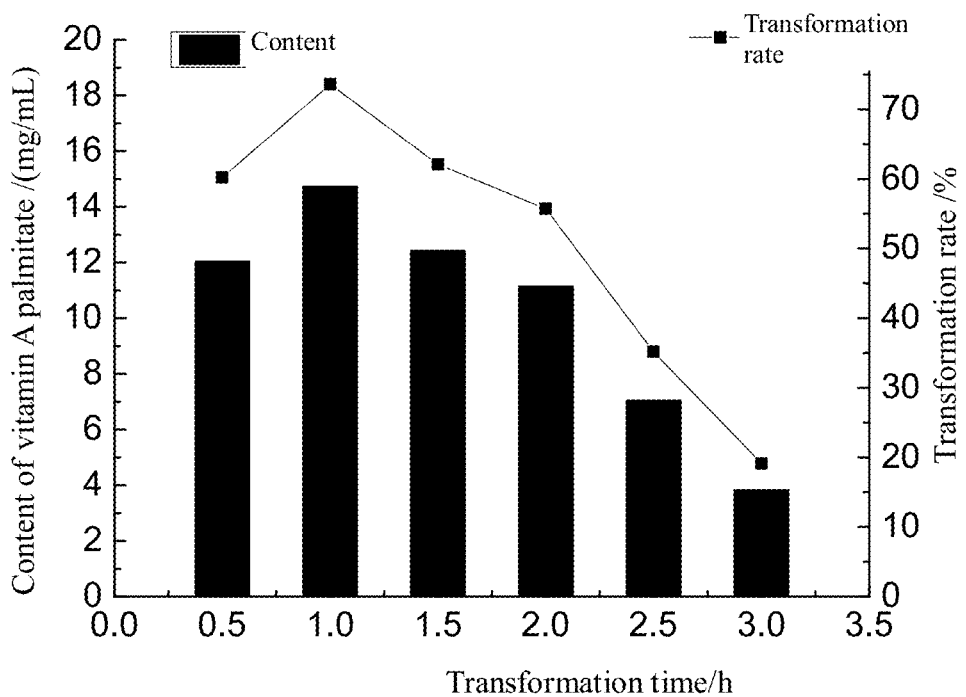
FIG. 4 shows the transformation time for production of vitamin A palmitate from *Bacillus subtilis* CS1802 by the whole-cell method.

This embodiment specifically describes the application of the strain CS1802 in the production of vitamin A palmitate through whole-cell transformation.
(1) inoculating the strain CS1802 into a beef extract peptone liquid medium for shake culture at 30° C. for 18~24 h;
(2) inoculating the strain cultured at the step (1) in an inoculum size of 2% into a fermentation medium for shake culture at 30° C. for 14~24 h; and centrifuging the fermentation broth, discarding the precipitate and collecting the supernatant.
(3) centrifuging the fermented bacterial solution at 3,000 r/min for 5 min, inoculating the bacteria at 25 g/L into an organic phase system (vitamin A: palmitic acid=10 g: 10 g dissolved in 1 L of n-hexane) for fermentation for 0.5 h, 1 h, 1.5 h, 2 h, 2.5 h and 3 h, then determining the content of vitamin A palmitate and calculating the transformation rate. From FIG. 4, it can be known that when the amount of bacteria added was 25 g/L, the highest transformation efficiency was 73.6% after 1 h of transformation, and the content of vitamin A palmitate was 14.72 mg/L.

Embodiment 5

Figure 5:
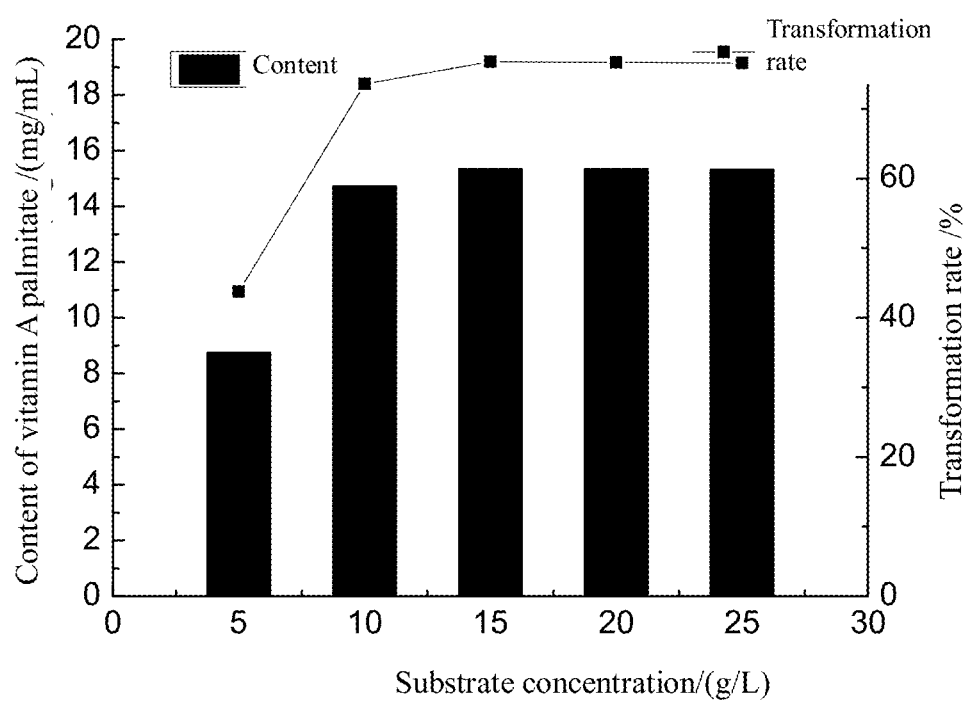
FIG. 5 shows the substrate concentration for production of vitamin A palmitate from *Bacillus subtilis* CS1802 by the whole-cell method.

This embodiment specifically describes the application of the strain CS1802 in the production of vitamin A palmitate through whole-cell transformation.
(1) inoculating the strain CS1802 into a beef extract peptone liquid medium for shake culture at 30° C. for 18~24 h;
(2) inoculating the strain cultured at the step (1) in an inoculum size of 2% into a fermentation medium for shake culture at 30° C. for 14~24 h; and centrifuging the fermentation broth, discarding the precipitate and collecting the supernatant.
(3) centrifuging the fermented bacterial solution at 3,000 r/min for 5 min, inoculating the bacteria at 25 g/L into an organic phase system with different substrate concentrations, i.e., vitamin A: palmitic acid=5 g:5 g, 10 g:10 g, 15 g:15 g, 20 g:20 g and 25 g:25 g, dissolving them in 1 L of n-hexane, respectively, fermenting for 1 h, then determining the content of vitamin A palmitate and calculating the transformation rate. From FIG. 5, it can be known that when the amount of bacteria added was 25 g/L and the organic system was vitamin A: palmitic acid=15 g:15 g, after dissolution in 1 L of culture medium and transformation for 1 h, the highest transformation efficiency was 76.75%, and the content of vitamin A palmitate was 15.35 mg/L.

The invention claimed is:

1. A method for production of vitamin A palmitate by a lipase-producing strain classified and named *Bacillus subtilis* CS 1802, with a deposit number of CCTCC NO: M2018262, the method comprising:
   (1) inoculating the strain CS1802 into a beef extract peptone liquid medium and culturing in a shaking apparatus;
   (2) inoculating the culture from step (1) into a fermentation medium, culturing in a shaking apparatus, centrifuging the fermentation broth, and collecting the supernatant as the fermented bacterial solution;
   (3) dissolving vitamin A and palmitic acid at a 1:1 mass ratio in n-hexane to produce an organic phase system; and
   (4) centrifuging the fermented bacterial solution from step (2) to collect the strain CS1802 and inoculating the strain CS1802 into the organic phase system from step (3) for fermentation to produce vitamin A palmitate.

2. The method according to claim 1, wherein the fermentation medium in step (2) consists of: tryptone 10 g/L, yeast powder 5 g/L, NaCl 10 g/L, $MgSO_4 \cdot 7H_2O$ 1 g/L, $KH_2PO_4$ 0.5 g/L, $K_2HPO_4$ 0.5 g/L, and olive oil emulsion 12 ml/L, wherein the olive oil emulsion is prepared by mixing polyvinyl alcohol (PVA) and olive oil at a volume ratio of 3:1.

3. The method according to claim 1, wherein each concentration of vitamin A and palmitic acid is 10-25 g/L, respectively.

4. The method according to claim 1, wherein the strain CS1802 are inoculated into the organic phase system and fermented for 0.5-2 hours in step (4).

5. The method according to claim 1, wherein each concentration of vitamin A and palmitic acid is 15 g/L, respectively.

6. The method according to claim 4, wherein the strain CS1802 are inoculated into the organic phase system and fermented for 1 hour in step (4).

* * * * *

SEQUENCE LISTING

```
<160> NUMBER OF SEQ ID NOS: 1

<210> SEQ ID NO 1
<211> LENGTH: 1387
<212> TYPE: DNA
<213> ORGANISM: Bacillus subtilis

<400> SEQUENCE: 1
cagtcgagcg gacagatggg agcttgctcc ctgatgttag cggcggacgg gtgagtaaca      60
cgtgggtaac ctgcctgtaa gactgggata actccgggaa accggggcta ataccggatg     120
gttgtttgaa ccgcatggtt caaacataaa aggtggcttc ggctaccact tacagatgga     180
cccgcggcgc attagctagt tggtgaggta acggctcacc aaggcgacga tgcgtagccg     240
acctgagagg gtgatcggcc acactgggac tgagacacgg cccagactcc tacgggaggc     300
agcagtaggg aatcttccgc aatggacgaa agtctgacgg agcaacgccg cgtgagtgat     360
gaaggttttc ggatcgtaaa gctctgttgt tagggaagaa caagtaccgt tcgaataggg     420
cggtaccttg acggtaccta accagaaagc cacggctaac tacgtgccag cagccgcggt     480
aatacgtagg tggcaagcgt tgtccggaat tattgggcgt aaagggctcg caggcggttt     540
cttaagtctg atgtgaaagc ccccggctca accggggagg gtcattggaa actggggaac     600
ttgagtgcag aagaggagag tggaattcca cgtgtagcgg tgaaatgcgt agagatgtgg     660
aggaacacca gtggcgaagg cgactctctg gtctgtaact gacgctgagg agcgaaagcg     720
tggggagcga acaggattag ataccctggt agtccacgcc gtaaacgatg agtgctaagt     780
```

-continued

```
gttaggggt    ttccgccct    tagtgctgca   gctaacgcat   taagcactcc   gcctggggag      840
tacggtcgca   agactgaaac   tcaaaggaat   tgacggggc    ccgcacaagc   ggtggagcat      900
gtggtttaat   tcgaagcaac   gcgaagaacc   ttaccaggtc   ttgacatcct   ctgacaatcc      960
tagagatagg   acgtcccctt   cggggcaga    gtgacaggtg   gtgcatggtt   gtcgtcagct     1020
cgtgtcgtga   gatgttgggt   taagtcccgc   aacgagcgca   acccttgatc   ttagttgcca    1080
gcattcagtt   gggcactcta   aggtgactgc   cggtgacaaa   ccggaggaag   gtggggatga    1140
cgtcaaatca   tcatgcccct   tatgacctgg   gctacacacg   tgctacaatg   gacagaacaa    1200
agggcagcga   aaccgcgagg   ttaagccaat   cccacaaatc   tgttctcagt   tcggatcgca    1260
gtctgcaact   cgactgcgtg   aagctggaat   cgctagtaat   cgcggatcag   catgccgcgg    1320
tgaatacgtt   cccgggcctt   gtacacaccg   cccgtcacac   cacgagagtt   tgtaacaccc    1380
gaagtcg                                                                        1387
```